United States Patent [19]

Schroeder et al.

[11] 4,261,908

[45] Apr. 14, 1981

[54] PROCESS FOR ISOLATING AROMATIC DINITRO COMPOUNDS

[75] Inventors: Bernd Schroeder, Odenthal; Bernd Thelen, Leverkusen; Wolfgang Auge, Cologne, all of Fed. Rep. of Germany; Karl-Werner Thiem, Charleston, S.C.

[73] Assignee: Bayer Aktiengesellschaft, Leverkusen, Fed. Rep. of Germany

[21] Appl. No.: 50,905

[22] Filed: Jun. 21, 1979

Related U.S. Application Data

[63] Continuation-in-part of Ser. No. 872,702, Jan. 26, 1978, abandoned.

[30] Foreign Application Priority Data

Feb. 4, 1977 [DE] Fed. Rep. of Germany ....... 2704680

[51] Int. Cl.$^3$ .................... C07C 50/18; C07C 79/10; C07C 79/121
[52] U.S. Cl. .................................. 260/369; 203/29; 568/931; 568/932; 568/933; 568/934
[58] Field of Search ...................... 203/13, 14, 29, 50, 203/53, 92, 96, 97, 34; 260/369, 645, 646; 568/931, 932, 933, 934

[56] References Cited

U.S. PATENT DOCUMENTS

| | | | |
|---|---|---|---|
| 1,309,577 | 7/1919 | Holmes | 260/645 |
| 2,739,174 | 3/1956 | Ross | 260/645 |
| 3,065,277 | 11/1962 | Hyman et al. | 260/645 |
| 3,780,116 | 12/1973 | Sahgal | 260/645 |
| 3,836,547 | 9/1974 | Toth | 260/369 |
| 3,836,601 | 9/1974 | Frey et al. | 260/369 |
| 3,928,475 | 12/1975 | Dassel | 260/645 |
| 4,031,116 | 6/1977 | Thiem | 260/369 |
| 4,045,455 | 8/1977 | Vogel | 260/369 |

*Primary Examiner*—Leland A. Sebastian
*Attorney, Agent, or Firm*—Sprung, Felfe, Horn, Lynch & Kramer

[57] ABSTRACT

A process has been developed for isolating aromatic dinitro compounds by using nitric acid in specified concentrations in different portions of a rectifying column and separating off the mixture of aromatic dinitro compounds from the sump of the rectifying column.

9 Claims, No Drawings

PROCESS FOR ISOLATING AROMATIC DINITRO COMPOUNDS

This application is a continuation-in-part of application Ser. No. 872,702 filed Jan. 26, 1978, now abandoned. p The present invention relates to a process for isolating aromatic dinitro compounds.

It is known that certain aromatic dinitro compounds can be obtained by nitrating aromatic compounds with highly concentrated nitric acid. For example, the preparation of dinitroanthraquinone from anthraquinone and/or 1-nitroanthraquinone or anthraquinone nitration mixtures and concentrated nitric acid (British Patent Specification No. 1,433,091) and of dinitrobenzene from benzene or nitrobenzene and concentrated nitric acid and of dinitrodiphenyl from diphenyl and nitric acid of density 1.45 are known (T. Urbanski, Chemistry and Technology of Explosives, Volume I, Warsaw 1964). Nitric acid is employed in excess here.

The dinitro compounds either crystallise out of these nitration mixtures and can be separated off directly by filtration, or they must be precipitated by special operations and then separated off.

This can be effected, for example, by diluting the reaction mixture with relatively large amounts of ice or water and isolating the dinitro compounds which have precipitated. Nitric acid is thereby obtained in a very dilute form and can no longer be concentrated in an economical manner to such an extent that it can be re-used for nitrations using highly concentrated nitric acid.

It is known from British Patent Specification No. 1,433,091 that in the dinitration of anthraquinone using concentrated nitric acid, 1,5- and/or 1,8-dinitroanthraquinone can be crystallised by distilling off nitric acid.

In general, a disadvantage of this process is that the weight ratio of nitric acid and water on the one hand to organic products on the other hand can be very greatly reduced in the evaporator of this installation. If this ratio is too greatly reduced, special process and safety measures can become necessary and thus, in certain circumstances, cause considerable additional expenditure.

Only a small amount of literature with respect to dinitrations of aromatic compounds other than anthraquinone using highly concentrated nitric acid and to the working up of such nitration mixtures exists. Such compounds, for example benzene, toluene, naphthalene, chlorobenzene, dichlorobenzene and similar compounds, are usually nitrated with mixed acids or with less highly concentrated nitric acid. However, it is difficult and expensive to work up mixed acids into a form which can be re-used. In addition, there is a prejudice against using highly concentrated nitric acid for the nitration of such compounds because it has been disclosed that a mixture of nitrobenzene, nitric acid and water detonated in an installation for the nitration of benzene using 65 to 70% strength nitric acid (see Chem. Eng. May 9th, 1966, page 163 and Chem. Eng. News Nov. 28th, 1960, page 47).

A process has now been found for isolating aromatic dinitro compounds from nitration mixtures obtained by nitrating aromatic compounds with nitric acid, which is characterised in that the nitration mixtures, which have been obtained in the nitration of aromatic compounds using nitric acid in a concentration above the concentration of the azeotropic acid, are fed into the rectifying region of a rectifying column, nitric acid which is more concentrated than that present in the feed mixture is taken off at the head, a nitric acid concentration in the range from about 66 to 88% by weight, but a lower nitric acid concentration than in the feed nitration mixture, is maintained in the sump of the column, and a mixture of aromatic dinitro compounds and nitric acid, from which the aromatic dinitro compounds are separated off, is removed from the sump of the rectifying column, a feed nitration mixture which has a nitric acid concentration above the azeotropic acid being used and in the rectifying column, as a function of the concentration of the particular nitric acid present, the weight ratio of the mixture of nitric acid and water, on the one hand, to organic constituents, on the other hand, being maintained at at least 3.5 when azeotropic nitric acid is present and at at least 9 when 100% strength nitric acid is present.

In general and as used herein, azeotropic acid or azeotropic nitric acid is understood as a nitric acid azeotrope with water with a concentration of 67.4% by weight nitric acid (compare Coll. Czech. Chem. Commun 25, 579–582 (1960). This concentration holds for 760 mm Hg. However, it can vary between 65 and 68% by weight, depending on the pressure conditions.

Those nitration mixtures in which, as a function of the concentration of the particular nitric acid present (which concentration is always above the aceotropic concentration), certain weight ratios of a mixture of nitric acid and water on the one hand to organic constituents on the other hand are maintained during the nitration are advantageously employed in the process according to the invention. The weight ratio is defind as follows: the weight of nitric acid present, calculated as 100% strength nitric acid, is added to the weight of water present, which can have been introduced with the nitric acid and can have been formed during the nitration, and this sum is divided by the total weight of organic constituents present. The organic constituents include, in particular, the aromatic compound added or unreacted and the nitration products of the aromatic compound. In the following text, the expression "weight ratio" is always understood as the weight ratio defined above.

The value below which the weight ratio in the nitration mixture should not fall is 3.5 when azeotropic nitric acid is present and 9 when 100% strength nitric acid is present. To a first approximation, a linear dependence of the value below which the weight ratio should not fall, on the acid concentration can be assumed between these two acid concentrations. On exact analysis, this dependence is not strictly linear but is somewhat more greatly pronounced at higher acid concentrations than at lower acid concentrations.

The reaction is preferably carried out so that the weight ratios in the nitration mixture are not the given weight ratios but are somewhat higher. For example, when 70% strength nitric acid is present the weight ratio can be at least 4, when 100% strength nitric acid is present it can be at least 10 and when the nitric acid concentrations are between these two values the weight ratio can have corresponding intermediate values. A precise knowledge of the small deviations of the value below which the weight ratio should not fall and of the acid concentration is therefore not absolutely necessary. The upper limit of the weight ratio is not critical. In general, it is 25, which is appropriate for economic reasons.

Briefly described, the accompanying figure is a schematic representation of an apparatus for carrying out the process according to the present invention.

The nitration mixture is worked up according to the invention in a rectifying column. A rectifying column of any desired form can be used for this, for example a tray column, packed column or trickle film column. Those rectifying columns such as are customarily used for isolating highly concentrated nitric acid from nitric acid with a concentration above 66% by weight are particularly suitable. The rectifying column is operated by taking off at the head a more highly concentrated nitric acid than that in the nitration mixture fed in. It is advantageous to take off, at the head of the rectifying column, nitric acid of a concentration such as can be re-used for the nitration of the particular aromatic compound. It is thus advantageous to re-concentrate the nitric acid, which is being diluted during the nitration reaction by the water of reaction liberated, in the rectifying column to such an extent that the concentration of the nitric acid taken off at the head of the recitfying column corresponds to that of the nitric acid originally employed in the nitration. However, it is also possible to take off, at the head of the rectifying column, nitric acid of a higher concentration. The nitric acid taken off at the head of the rectifying column can also contain nitric oxides, such as $N_2O_5$, $N_2O_4$, $NO_2$ and/or $NO$.

The number of plates in the rectifying column to be used according to the invention depends on the acid concentration of the nitration mixture fed in and the desired concentration of the nitric acid to be taken off at the head. In general, rectifying columns which have 1–20 theoretical plates can be used. Rectifying columns with 2–15 theoretical plates are preferably used.

The feed point of the nitration mixture into the rectifying column depends on the concentration of the nitric acid in the nitration mixture and the concentration profile in the rectifying column. If the nitric acid taken off at the head of the rectifying column is to be re-used for the same nitration, in general it is necessary to only slightly concentrate the nitric acid present in the nitration mixture. In these cases, the nitration mixture can be fed onto one of the higher trays of the rectifying column, for example onto the highest or second highest tray of the rectifying column. If a greater concentrating of the nitric acid present in the nitration mixture is desired, the nitration mixture is advantageously fed in at a lower point in the rectifying region of the rectifying column.

The rectifying column is designed and operated so that a nitric acid of lower concentration than in the nitration mixture is present in the sump, but the concentration of the nitric acid in the sump does not fall below 66% by weight.

It is an essential aspect of the present invention that, as a function of the concentration of the particular nitric acid present, values of the weight ratios of mixtures of nitric acid and water on the one hand to organic constituents on the other hand should not fall below 3.5 (when azeotropic nitric acid and mononuclear aromatic compounds are present or when 75% strength by weight nitric acid and polynuclear aromatic compounds are present) to 9 (when 100% strength by weight nitric acid and mononuclear or polynuclear aromatic compounds are present) at all points of the rectifying column during the working up by distillation. The upper limit of the weight ratio is not essential for the working up according to the invention. A weight ratio of 25 is favourable for economic reasons. No particular attention must be paid here to the part of the rectifying column in which the concentrating of the nitric acid takes place, which is the part between the addition point of the nitration mixture and the head of the rectifying column. Higher weight ratios than in the nitration mixture are unavoidably set up in this part of the apparatus. Below the addition point of the nitration mixture, in particular in the sump of the rectifying column, concentrating of the organic constituents takes place, with simultaneous expulsion of nitric acid. The weight ratio thus falls here.

If a relatively dilute nitric acid, for example a nitric acid in the concentration range from about 70 to 90% by weight, and a relatively high weight ratio, for example a weight ratio above 10 (in the case of nitric acid concentrations in the range from about 70–80% by weight) or of over 15 (in the case of a nitric acid concentration in the range from about 80–90% by weight) is present in the nitration mixture to be worked up, in general no particular measures are required in order that the weight ratios do not fall below the abovementioned values in the lower region and in the sump of the rectifying column.

However, if other nitration mixtures are to be worked up, for example nitration mixtures in which nitric acid with a concentration in the range from about 68 to 85% by weight and a relatively low weight ratio, for example a weight ratio below 10, are present, or nitration mixtures in which concentrated nitric acid, for example about 85 to 100% strength nitric acid, and a weight ratio below 15, are present, it is in general necessary to take particular measures so that the weight ratio as far as possible does not fall below the abovementioned values in the lower part or in the sump of the rectifying column. In these cases, too great a lowering of the weight ratio can be avoided by adding, below the addition point of the nitration mixture, water or nitric acid with a concentration below that in the nitration mixture. It must be ensured here that enough water or nitric acid is added so that the weight ratio does not fall below the abovementioned values at any point of the rectifying column. If nitric acid with a concentration above 66% by weight is added, there is no upper limit on the amount of nitric acid added. If water or nitric acid with a concentration below 66% by weight is added, it must be ensured that the sum of all the column feeds gives a mixture with a nitric acid concentration above 66% by weight. The water or nitric acid can be added at any desired point below the addition point of the nitration mixture, for example in the sump of the rectifying column. If the addition is to take place in the rectifying region of the rectifying column, it is advantageous to add nitric acid with a concentration which deviates by a maximum of ±5% by weight from the concentration of the nitric acid which is present at the addition point in the rectifying column without the addition of the nitric acid. In this manner, the rectification in the column is not excessively interfered with.

Independently of whether or not water or nitric acid is additionally fed in, the rectifying column can be operated under normal pressure, reduced pressure or slightly elevated pressure. In general, it is operated under pressures in the range from about 50 to 760 mm Hg, preferably under pressures in the range from about 50 to 500 mm Hg. The temperature at which the rectifying column is operated depend on the pressure in the rectifying column, on the concentration of the nitric acid in the nitration mixture and on the concentration of the nitric acid taken off at the head of the rectifying column.

The reflux ratio (ratio of the liquid reflux to the take-off of the concentrated nitric acid) of the rectifying column can be varied within wide limits. For example, the reflux ratio can be between 0 to 5. Reflux ratios between 0.1 to 1 are preferred. The concentration of the appropriately refluxing nitric acid can be higher than or have the same value as the acid concentration on the tray onto which the recycled acid runs back.

The aromatic dinitro compounds are separated off from the bottom outflow of the rectifying column.

If the process according to the invention is used for isolating dinitroanthraquinones which has been obtained by nitrating anthraquinone and/or 1-nitroanthraquinone or anthraquinone nitration mixtures with nitric acid having a concentration in the range from about 92 to 100% by weight, the procedure can be such that the nitration mixture is fed into the rectifying region of a rectifying column, nitric acid which is more concentrated than that present in the feed mixture is taken off at the head, a nitric acid concentration in the range from about 66 to 88% by weight, but a lower nitric acid concentration than in the feed nitration mixture, is maintained in the sump of the column and a mixture of dinitroanthraquinone and nitric acid, from which the dinitroanthraquinones are separated off, is removed from the sump of the rectifying column, in the rectifying column, as a function of the concentration of the particular nitric acid present, the weight ratio of the mixture of nitric acid and water, on the one hand, to organic constituents, on the other hand, being maintained in the range from 3.5 to 25, if azeotropic nitric acid is present, and in the range from 9 to 25, if 100% strength nitric acid is present.

In an industrial embodiment of the process according to the invention for isolating dinitroantronthroquinones, the procedure is as follows: antraquinone and/or 1-nitroanthraquinone or an anthraquinone nitration mixture is nitrated with at least 92% strength nitric acid. Enough nitric acid is employed here so that at the start of the nitration the weight ratio of nitric acid and water on the one hand to anthraquinone on the other hand is at least 10 when 92% strength nitric acid is employed and at least 13 when 99.5% strength nitric acid is employed. Referring now to the attached figure, the nitration is carried out at about 20° to 70° C. After the nitration, the nitration mixture is fed via inlet (2) into the upper half of a rectifying column (1) which contains a total of 3 to 15 theoretetical plates. The rectifying column is operated under a pressure in the range from about 80 to 300 mm Hg. Nitric acid of the same concentration as is employed for the nitration, or nitric acid of a higher concentration, is taken off at the head of the column via outlet (4). The reflux ratio at the head of the column is between 0.1 and 1. By adding water or nitric acid with a concentration below 82% by weight to the sump of the rectifying column or adding nitric acid with a concentration in the range from about 68 to 90% by weight to the rectifying region of the column below the addition point of the nitration mixture via inlet (3), it is ensured that the value of the weight ratio of nitric acid and water on the one hand to organic constituents on the other hand as far as possible does not fall below 3.5 (when 68% strength nitric acid is present) and 9 (when 100% strength nitric acid is present) at no point of the rectifying column (including the sump). The addition of water or nitric acid and the operation of the rectifying column is controlled here so that a nitric acid concentration in the range from about 66 to 88% by weight, but a nitric acid concentration which is lower than that in the nitration mixture by at least 10% absolute, is set up in the sump. The bottom outflow of the rectifying column via outlet (5) is cooled to about to 20° to 40° C. and the dinitroanthraquinones are separated off by filtration or centrifugation in the separation unit (6) from which are removed, via outlet (7), the aromatic dinitro compound and, via outlet (8), the mother liquor.

When the process according to the invention is used for isolating dinitro derivatives of monocyclic or bicyclic carbocyclic aromatic hydrocarbons, optionally substituted by chlorine atoms, such as benzene, toluene, naphthalene, chlorobenzene, dichlorobenzene and diphenyl from nitration mixtures which have been obtained by nitrating benzene, toluene, naphthalene, chlorobenzene, dichlorobenzene and diphenyl with nitric acid having a concentration in the range from about 70 to 100% by weight, the procedure can preferably be such that the nitration mixture is fed into the rectifying region of a rectifying column with 1 to 20 theoretical plates, nitric acid which is more concentrated than that present in the feed mixture is taken off at the head, a nitric acid concentration in the range from about 66 to 88% by weight, but a lower nitric acid concentration than in the feed nitration mixture, is maintained in the sump of the column and a mixture of dinitrobenzene, dinitrotoluene, dinitronaphthalene, dinitrochlorobenzene or dinitrodiphenyl and nitric acid, from which the abovementioned aromatic dinitro compounds are separated off, is removed from the sump of the rectifying column, in the rectifying column, as a function of the concentration of the particular nitric acid present, the weight ratio of the mixture of nitric acid and water on the one hand to organic constituents on the other hand is maintained in the range from 4 to 25, when 70% strength nitric acid is present, and in the range from 11 to 25, when 100% strength nitric acid is present.

The process according to the invention has the following advantages: although the process can be carried out in concentrated nitric acid, special process or safety measures can be dispensed with. The nitration mixture can be worked up in a relatively simple rectifying column in which suitable conditions for separating off the aromatic dinitro compounds are achieved.

It was surprising that it is possible to isolate aromatic dinitro compounds by the process according to the invention at low weight ratios of about 3.5 (when azeotropic nitric acid is present) and 9 (when 100% strength nitric acid is present). The weight ratios are thus almost identical to those which are to be maintained in the isolation of aromatic mononitro compounds. Rather, it was to be expected that expensive process and safety measures would be necessary for the isolation of aromatic dinitro compounds at low weight ratios.

The aromatic dinitro compounds isolated by the process according to the invention can be used as intermediate products for the preparation of dyestuffs, plant protection agents and pharmaceuticals (literature: Colour Index 65,405, 65,415 and 70,510; and Chemistry and Technology of Explosives, Volume I, T. Urbanski, Warsaw 1964). The process according to the invention is particularly suitable for preparing crystalline mixtures of 1,5- and 1,8-dinitroanthraquinone. These mixtures can either be used directly as intermediate products for the preparation of dyestuffs, but it is also possible to separate the isomers into virtually pure 1,5-dinitroanthraquinone and virtually pure 1,8-dinitroanthraquinone by crystallisation from organic solvents, for example from sulpholane, 1-chloronaphthalene, adipodinitrile, nitrobenzene, nitrotoluene, phenol, pyridones or N-methylpyrrolidone, and to use the virtually pure isomers as intermediate products for the preparation of dyestuffs.

EXAMPLE 1

3.49 kg of anthraquinone (99% pure) were nitrated with 49.50 kg of 98.3% strength nitric acid for 1 hour at 50° to 55° C.

5.00 kg of this dinitroanthraquinone mixture (consisting of 41.2% of 1,5-dinitroanthraquinone, 39.6% of 1,8-dinitroanthraquinone, 8.9% of 1,6-dinitroanthraquinone and 9.5% of 1,7-dinitroanthraquinone) together with 49.04 kg of 97 percent strength by weight nitric acid (molar ratio 45) continuously flow, per hour, onto the fourth tray of a 5-tray rectifying column at about 55° C. 29.65 kg/hour of 99 percent strength by weight nitric acid is taken off at the head of the column at a reflux ratio of reflux/take-off of 0.4. The column is operated under a head pressure of 200 mm Hg, a head temperature of about 50° C. being set up. 19.29 kg/hour of 70 percent strength by weight nitric acid are continuously added to the sump of the column at a temperature of about 70° C. The dinitro-anthraquinone mixture to be crystallised, in which the molar ratio of nitric acid to organic products is 30:1 and the nitric acid concentration is 82 percent by weight (weight ratio 7.7), is removed at the sump of the column at a temperature of about 70° C. 3.8 kg per hour of a dinitroanthraquinone mixture having a composition of 53.2% of 1,5-dinitroanthraquinone, 44.6% of 1,8-dinitroanthraquinone, 0.3% of 1,6-dinitroanthraquinone and 1.8% of 1,7-dinitroanthraquinone is isolated from the mixture thus obtained, by cooling to room temperature (25° to 30° C.), separating off by filtration the solid which has precipitated and then drying it.

EXAMPLE 2

3.93 kg of a mixture of 50.1% anthraquinone, 18.9% 1-nitroanthraquinone, 12.0% 2-nitroanthraquinone, 9.0% 1,5-di-nitroanthraquinone, 7.2% 1,8-dinitroanthraquinone, 1,4% 1,6-dinitroanthraquinone and 1,4%, 1,7-dinitroanthraquinone were nitrated with 50.10 kg 98% strength nitric acid for 1 hour at 50° C.

5.00 kg of this dinitroanthraquinone mixture (consisting of 39.0% of 1,5-dinitro-anthraquinone, 35.5% of 1,8-dinitroanthraquinone, 12.4% of 1,6-dinitroanthraquinone, 12.1% of 1,7-dinitroanthraquinone and 0.8% of 2,6-dinitroanthraquinone) together with 49.04 kg of 97 percent strength by weight nitric acid (molar ratio 45) are continuously fed, per hour, onto the highest tray of a rectifying column with a total of 10 trays. The column is operated under a pressure of 200 mm Hg and with a reflux ratio of reflux to take-off of 0.5. 35.94 kg/hour of 99 percent strength by weight nitric acid are taken off at the head of the rectifying column. 43.27 kg/hour of 70 percent strength by weight nitric acid are fed in above the sump. A product mixture which has a nitric acid concentration of 75 percent by weight and a molar ratio of nitric acid to organic products of 40 (weight ratio 11.3) is removed at the sump of the column. The amount of nitric acid removed per hour is 56.37 kg. 4.22 kg per hour of a mixture consisting of 41.2% of 1,5-dinitroanthraquinone, 37.7% of 1,8-dinitroanthraquinone, 9.0% of 1,6-dinitroanthraquinone and 11.3% of 1,7-dinitroanthraquinone are isolated by cooling the bottom outflow to 25° to 30° C. and filtering off and drying the solid.

EXAMPLE 3

5.00 kg of a dinitroanthraquinone mixture (composition as in Example 2) together with 59.81 kg of 97.2 percent strength by weight nitric acid (molar ratio 55) are fed per hour onto the third tray of a 5-tray rectifying column. The column is operated under a head pressure of 200 mm Hg. By taking off 39.78 kg/hour of 99 percent strength by weight nitric acid at the head of the column at a reflux ratio of reflux to take-off of 0.4 and adding 25.45 kg/hour of 80 percent strength by weight nitric acid to the sump of the column, a nitric acid concentration of 86 percent by weight and a molar ratio of nitric acid to organic products of 37 (weight ratio 9.1) are set up. 2.82 kg of a dinitroanthraquinone mixture having a composition of 60.2% of 1,5-dinitroanthraquinone, 39.2% of 1,8-dinitroanthraquinone, 0.2% of 1,6-dinitroanthraquinone and 0.4% of 1,7-dinitroanthraquinone are isolated per hour from the sump after cooling to 25° to 30° C. and separating off and drying the solid which has crystallised out.

EXAMPLE 4

3.53 kg of anthraquinone (97% pure) were nitrated with 77.03 kg of 97.5% strength nitric acid for 1 hour at 45° C. 5.00 kg of this dinitration mixture having a composition of 40.9% of 1,5-dinitroanthraquinone, 39.8% of 1,8-dinitroanthraquinone, 7.2% of 1,6-dinitroanthraquinone and 7.7% of 1,7-dinitroanthraquinone together with 76.28 kg of 97 percent strength by weight nitric acid are continuously fed, per hour, onto the fourth tray of a 5-tray rectifying column at about 55° C. The column is operated under a head pressure of 200 mm Hg. 48.18 kg/hour of 99 percent strength by weight nitric acid are taken off at the head of the column at a reflux ratio of reflux/take-off of 0.2. The head temperature in the column is about 50° C. 45.49 kg/hour of 70 percent strength by weight nitric acid at about 70° C. are continuously added to the sump. The mixture to be crystallised, in which the molar ratio of nitric acid to dinitroanthraquinones is 55 and the acid concentration is 79 percent by weight (weight ratio 14.7), is removed at the sump at a temperature of about 70° C. The amount of nitric acid thereby removed is 73.59 kg/hour. The mixture is allowed to cool to room temperature and the solid which has crystallised out is filtered off and dried. 3.70 kg of a dinitroanthraquinone mixture having a composition of 51.8% of 1,5-dinitroanthraquinone, 46.5% of 1,8-dinitroanthraquinone, 0.4% of 1,6-dinitroanthraquinone and 1.2% of 1,7-dinitroanthraquinone are isolated per hour.

EXAMPLE 5

The reaction mixture to be crystallised, consisting of 5.00 kg of dinitroanthraquinone (composition as in Example 2) and 76.28 kg of 97 percent strength by weight nitric acid (molar ratio 70) is fed per hour onto the 6th tray of an 8-tray rectifying column operated under 200 mm Hg and at a reflux ratio of 0.2. 55.52 kg/hour of 99 percent strength by weight nitric acid are removed at the head of the column and 46.01 kg/hour of water are added to the sump. A product mixture which has a nitric acid concentration of 75 percent by weight and a molar ratio of 18 (weight ratio 5.1) is removed at the sump of the column. By lowering the temperature to 25° to 30° C. and filtering off the solid, 4.33 kg/hour of a product mixture having a composition of 40.8% of 1,5-dinitro-anthraquinone, 37.2% of 1,8-dinitroanthraquinone, 10.2% of 1,6-dinitro-anthraquinone and 11.9% of 1,7-dinitroanthraquinone are obtained after drying.

EXAMPLE 6

500 kg/hr of a dinitroanthraquinone mixture (composition as in Example 2) together with 101.2 kg/hour of 94 percent strength by weight nitric acid (molar ratio 90) are fed onto the 4th tray of a 13-tray rectifying column which is operated under a head pressure of 200 mm Hg and at a reflux ratio of 0.6. 83.33 kg/hour of 99.5 percent strength by weight nitric acid is taken off at the head of the column. The dinitroanthraquinone mixture to be crystallised, in which the molar ratio of nitric acid to organic products is 12.5 and the nitric acid concentration is 70 percent by weight (weight ratio 3.8), is removed at the sump of the column. The dinitroanthraquinone mixture added is almost quantitatively recovered from the mixture thus obtained, by cooling to 25° to 30° C., filtering off the solid which has precipitated and then drying it.

EXAMPLE 7

A solution of 100 g of dinitrobenzene (~88 percent by weight of 1,3-dinitrobenzene, 10 percent by weight of 1,2-dinitrobenzene and 2 percent by weight of 1,4-dinitrobenzene) in 900 g of 95% strength nitric acid is continuously fed, per hour, at about 55° C. onto the fourth tray of a 5-tray rectifying column, into the sump of which 276 g/hour of 70 percent strength by weight nitric acid are fed and from which 776 g/hour of 99 percent strength by weight nitric acid is removed via the head. In the sump of the column there results an acid concentration of 70% nitric acid and a weight ratio of acid to solid of 4:1. 66.7 g/hour of water are fed to the bottom outflow obtained at a temperature of about 70° C., so that an approximately 60% strength acid (weight ratio of acid/solid: ~4.7) is formed.

After cooling the bottom outflow to room temperature, the dinitrobenzene, which crystallises out almost quantitatively, is filtered off, washed with water until neutral and dried.

What is claimed is:

1. Process for isolating aromatic dinitro compounds from nitration mixtures obtained by nitrating aromatic compounds with nitric acid, which comprises feeding, into the rectifying region of a rectifying column, a nitration mixture, which has been obtained in the nitration of aromatic compounds using nitric acid in a concentration above the concentration of the azeotropic acid, taking off at the head nitric acid which is more concentrated than that present in the feed mixture, maintaining a nitric acid concentration in the range from 66 to 88% by weight, but a lower nitric acid concentration than in the feed nitration mixture, in the sump of the column, removing from the sump of the rectifying column a mixture of aromatic dinitro compounds and nitric acid, from which the aromatic dinitro compounds are separated off, a feed nitration mixture which has a nitric acid concentration above the azeotropic acid being used and in the rectifying column, as a function of the concentration of the particular nitric acid present, a weight ratio of the mixture of nitric acid and water, on the one hand, to organic constituents, on the other hand, being maintained in the range from 3.5 to 25 when azeotropic nitric acid is present and in the range from 9 to 25 when 100% strength nitric acid is present.

2. Process according to claim 1, characterized in that water or nitric acid with a concentration below that in the nitration mixture is added to the rectifying column below the addition point of the nitration mixture.

3. Process according to claim 2, characterized in that water or nitric acid with a lower concentration than that in the nitration mixture is added to the sump of the rectifying column.

4. Process according to claim 2, characterized in that nitric acid with a concentration which deviates by a maximum of ±5% by weight from the concentration of the nitric acid which is present at the addition point in the rectifying column without the addition of nitric acid is added to the rectifying region of the rectifying column below the addition point of the nitration mixture.

5. Process according to claim 1, characterized in that nitric acid with a concentration which can be re-used for the nitration of the particular aromatic compound is taken off at the head of the rectifying column.

6. Process according to claim 1, characterized in that a rectifying column which has 1 to 20 theoretical plates is used.

7. Process according to claim 1, characterized in that the rectifying column is operated under a pressure in the range from about 50 to 760 mm Hg.

8. Process for isolating dinitroanthraquinones which have been obtained by nitrating (1) anthraquinone or (2) 1-nitroanthraquinone (3) a mixture of anthraquinone and 1-nitroanthraquinone (4) anthraquinone nitration mixtures with nitric acid having a concentration in the range from 92 to 100% by weight, which comprises taking off at the head nitric acid which is more concentrated than that present in the feed mixture, maintaining in the sump of the column a nitric acid concentration in the range from 66 to 88% by weight, but a lower nitric acid concentration than in the feed nitration mixture, and removing from the sump of the rectifying column a mixture of dinitroanthraquinones and nitric acid, from which the dinitroanthraquinones are separated off, in the rectifying column, as a function of the concentration of the particular nitric acid present, the weight ratio of the mixture of nitric acid and water, on the one hand, to organic constituents, on the other hand, being maintained in the range from 3.5 to 25, if azeotropic nitric acid is present, and in the range from 9 to 25, if 100% strength nitric acid is present.

9. Process for isolating dinitro derivatives of benzene, toluene, naphthalene, chlorobenzene, dichlorobenzene and diphenyl from nitration mixtures which have been obtained by nitrating benzene, toluene, naphthalene, chlorobenzene, dichlorobenzene and diphenyl, respectively, with nitric acid having a concentration in the range from 70 to 100% by weight, which comprises feeding the nitration mixture into the rectifying region of a rectifying column with 1 to 20 theoretical plates, taking off at the head nitric acid which is more concentrated than that present in the feed mixture maintaining in the sump of the column, a nitric acid concentration in the range from 66 to 88% by weight, but a lower nitric acid concentration than in the feed nitration mixture, and removing from the sump of the rectifying column a mixture of dinitrobenzene, dinitrotoluene, dinitronaphthalene, dinitrochlorobenzene or dinitrodiphenyl and nitric acid, from which the abovementioned aromatic dinitro compounds are separated off, in the rectifying column, as a function of the concentration of the particular nitric acid present, the weight ratio of the mixture of nitric acid and water on the one hand to organic constituents on the other hand is maintained in the range from 4 to 25, when 70% strength nitric acid is present, and in the range from 11 to 25, when 100% strength nitric acid is present.

* * * * *